US012102725B2

(12) United States Patent
Onishi et al.

(10) Patent No.: US 12,102,725 B2
(45) Date of Patent: Oct. 1, 2024

(54) ENDOSCOPE REPROCESSOR AND BOTTLE

(71) Applicant: OLYMPUS CORPORATION, Tokyo (JP)

(72) Inventors: Hideto Onishi, Hachioji (JP); Eiri Suzuki, Sagamihara (JP); Yumiko Awau, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 823 days.

(21) Appl. No.: 17/131,951

(22) Filed: Dec. 23, 2020

(65) Prior Publication Data

US 2021/0106706 A1  Apr. 15, 2021

Related U.S. Application Data

(63) Continuation of application No. PCT/JP2018/025063, filed on Jul. 2, 2018.

(51) Int. Cl.
*A61B 1/12* (2006.01)
*A61L 2/18* (2006.01)

(52) U.S. Cl.
CPC ............... *A61L 2/18* (2013.01); *A61B 1/12* (2013.01); *A61L 2202/121* (2013.01); *A61L 2202/123* (2013.01); *A61L 2202/15* (2013.01); *A61L 2202/24* (2013.01)

(58) Field of Classification Search
CPC ....... A61B 1/12; A61L 2/18; A61L 2202/121; A61L 2202/123; A61L 2202/15; A61L 2202/24
See application file for complete search history.

(56) References Cited

U.S. PATENT DOCUMENTS 6,379,632 B1   4/2002  Kinoshita et al.
8,246,909 B2 *  8/2012  Williams ................. A61L 2/24
                                                             73/36
(Continued)

FOREIGN PATENT DOCUMENTS

CN    107427203 A    12/2017
JP     52-18222 A     2/1977
(Continued)

OTHER PUBLICATIONS

International Search Report dated Sep. 4, 2018 issued in PCT/JP2018/025063.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope reprocessor includes a bottle connecting instrument and a nozzle. The bottle connecting instrument includes a first advancing and retracting member which shuts off a first flow path at a first position and opens the first flow path at a second position; a first fitting member; and a first retaining member which retains the first advancing and retracting member. The nozzle includes a second advancing and retracting member which shuts off the nozzle at a third position and opens the nozzle at a forth position, a second fitting member to be fitted with the first fitting member, and a second retaining member which retains the second advancing and retracting member.

12 Claims, 13 Drawing Sheets

(56) References Cited

U.S. PATENT DOCUMENTS

2013/0118537 A1* 5/2013 Komiya ................ A61B 1/121
                                                    134/166 C
2013/0125934 A1* 5/2013 Komiya ................ A61B 1/123
                                                    134/166 C
2017/0100026 A1* 4/2017 Inoue .................... A61B 1/123
2017/0143197 A1* 5/2017 Onishi .................. A61B 1/125

FOREIGN PATENT DOCUMENTS

| JP | 57-174889 U | 11/1982 |
| --- | --- | --- |
| JP | H3-60684 U | 6/1991 |
| JP | H7-18614 Y2 | 5/1995 |
| JP | 2000-287924 A | 10/2000 |
| JP | 2003-111725 A | 4/2003 |
| JP | 2006-230493 A | 9/2006 |
| JP | 2018-438 A | 1/2018 |

* cited by examiner

ENDOSCOPE REPROCESSOR AND BOTTLE

CROSS REFERENCE TO RELATED APPLICATION

This application is a continuation application of PCT/JP2018/025063 filed on Jul. 2, 2018, the entire contents of which are incorporated herein by this reference.

BACKGROUND OF THE INVENTION

1. Field of the Invention

The present invention relates to an endoscope reprocessor and a bottle.

2. Description of the Related Art

Conventionally, there has been known an endoscope reprocessor which performs reprocessing processing such as cleaning and disinfecting of an endoscope used for a subject by using a medicinal solution such as a disinfection solution, a cleaning solution, alcohol or the like. The endoscope reprocessor is connected to a bottle in which a medicinal solution is stored, by a bottle connecting instrument, and a medicinal solution to be used for reprocessing processing is obtained from the bottle. In some cases, the bottle connecting instrument is brought into an open state where the bottle connecting instrument communicates with the inside of the bottle sealed when the bottle connecting instrument is connected to the bottle, whereas the bottle connecting instrument is brought into a closed state so as to prevent a leakage of residual solution when the bottle connecting instrument is removed from the bottle.

For example, Japanese Utility Model Application Publication No. H7-18614 discloses a connecting instrument including a female connector having a valve which closes a solution passing hole from below, and a male connector having a spring which biases a valve element in a direction that the valve element is pushed to a valve seat. When the male connector is removed from the female connector, not to mention that the male connector automatically closes, the female connector automatically closes a container and hence, a solution remaining in the bottle does not leak.

Further, there may be a case where a bottle connecting instrument is subjected to a water conduction test in an inspection step of the manufacturing of a bottle connecting instrument. When the bottle connecting instrument described in the Japanese Utility Model Application Publication No. H7-18614 is subjected to a water conduction test, in the water conduction test, the bottle connecting instrument is fixed using a jig or the like such that an open state is maintained in a state where the bottle connecting instrument is not connected to a bottle, and water is made to flow through the bottle connecting instrument, and the bottle connecting instrument is dried. When the inspection step is finished, the jig is removed from the bottle connecting instrument.

SUMMARY OF THE INVENTION

An endoscope reprocessor according to one aspect of the present invention includes: a main body apparatus including a suction pump, a tube having one end which communicates with the suction pump, and a bottle connecting instrument connected to another end of the tube; and a bottle including a medicinal solution storing chamber; and a nozzle which communicates with the medicinal solution storing chamber. The bottle connecting instrument includes: a connecting port which is connected to the tube; an insertion port into which a distal end of the nozzle is inserted; a first flow path which connects the connecting port and the insertion port with each other; a first advancing and retracting member which is disposed so as to be advanceable and retractable in the first flow path, the first advancing and retracting member being configured to shut off the first flow path when the first advancing and retracting member is positioned at a first position in the first flow path and open the first flow path when the first advancing and retracting member is positioned at a second position on a side of the connecting port with respect to the first position; a first fitting member disposed in the first advancing and retracting member on a side of the insertion port; and a first retaining member configured to retain the first advancing and retracting member when the first advancing and retracting member is positioned at the first position. The nozzle includes inside of the nozzle: a second advancing and retracting member which is disposed so as to be advanceable and retractable in the nozzle, the second advancing and retracting member being configured to shut off the nozzle when the second advancing and retracting member is positioned at a third position in the nozzle and open the nozzle when the second advancing and retracting member is positioned at a fourth position on a side of the medicinal solution storing chamber with respect to the third position; a second fitting member which protrudes from the second advancing and retracting member toward a nozzle opening of the nozzle, and is configured to be fitted with the first fitting member; and a second retaining member configured to retain the second advancing and retracting member when the second advancing and retracting member is positioned at the third position.

A bottle according to one aspect of the present invention is configured to be connected to a main body apparatus of an endoscope reprocessor and includes a medicinal solution storing chamber and a nozzle which communicates with the medicinal solution storing chamber. The nozzle includes inside of the nozzle: a second advancing and retracting member which is disposed so as to be advanceable and retractable in the nozzle, the second advancing and retracting member being configured to shut off the nozzle when the second advancing and retracting member is positioned at a third position in the nozzle and open the nozzle when the second advancing and retracting member is positioned at a fourth position on a side of the medicinal solution storing chamber with respect to the third position; a second fitting member which protrudes from the second advancing and retracting member toward a nozzle opening of the nozzle, and is configured to be fitted with a first fitting member included in the main body apparatus of the endoscope reprocessor; and a second retaining member configured to retain the second advancing and retracting member when the second advancing and retracting member is positioned at the third position.

DETAILED DESCRIPTION OF THE PREFERRED EMBODIMENT(S)

An embodiment of the present invention is described with reference to drawings.

Configuration

Figure 1:
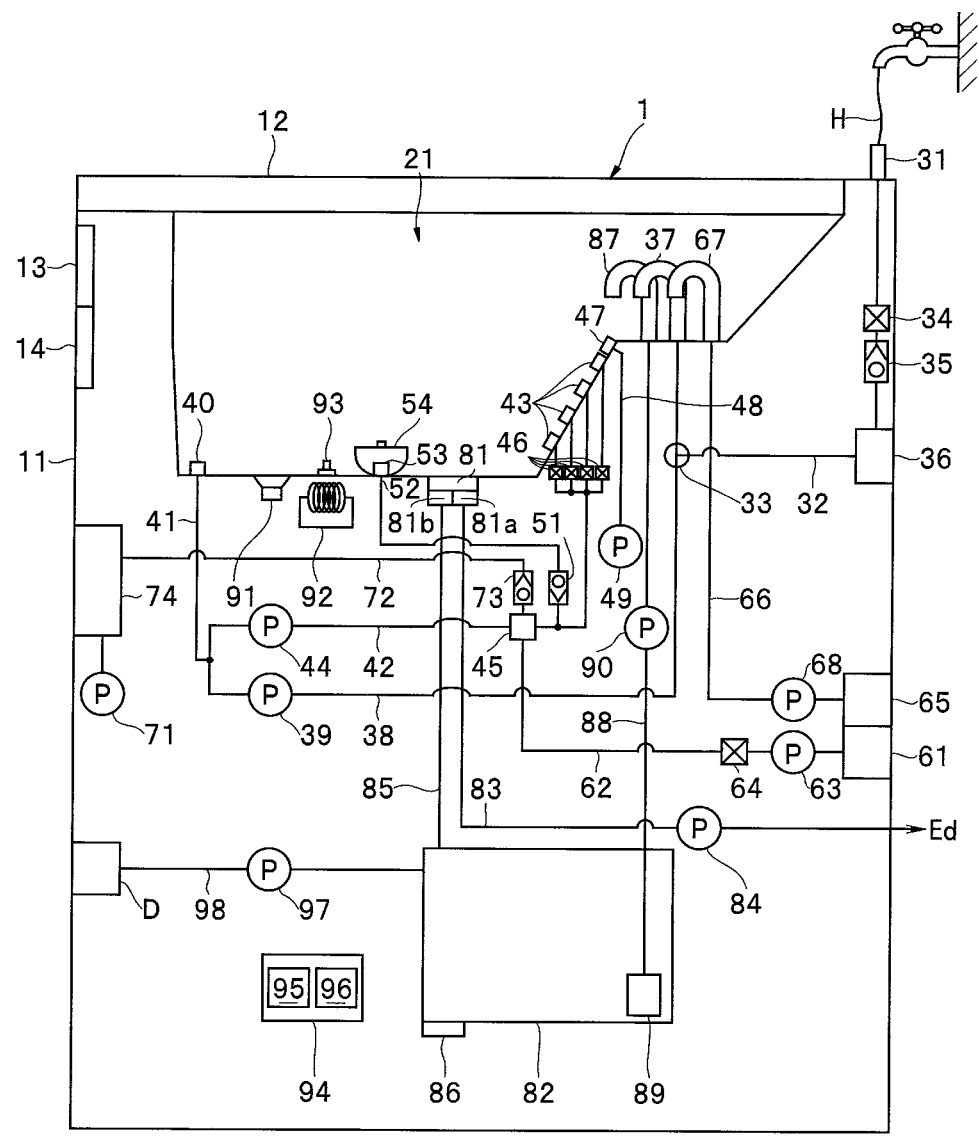
FIG. 1 is a block diagram showing one example of a configuration of an endoscope reprocessor according to an embodiment of the present invention.

FIG. 1 is a block diagram showing one example of a configuration of an endoscope reprocessor 1.

As shown in FIG. 1, the endoscope reprocessor 1 is a device which performs reprocessing processing of a contaminated endoscope, and parts, accessories and the like of the endoscope. In this specification, reprocessing processing is not particularly limited, and may be any of rinsing with water, cleaning for removing dirt such as organic substances, disinfection for making predetermined microorganism ineffective, sterilization for exterminating or killing all microorganisms, or may be a combination of these. Accessories are not particularly limited. Examples of the accessories include a suction button, an air/water feeding button, and a distal end cover which covers a distal end member of the endoscope, which are mounted on the endoscope in use and are removed from the endoscope at the time of performing reprocessing processing.

The endoscope reprocessor 1 includes a body unit 11 and a top cover 12.

The top cover 12 is mounted on an upper portion of the body unit 11 in an openable/closable manner. When the top cover 12 is opened, a processing tank 21 is exposed to an outside.

The body unit 11 is a main body apparatus and includes a display panel 13 and an operation panel 14. The display panel 13 can display various types of information under a control of a control unit 94. The operation panel 14 is used for a user to input instructions. When the user inputs instructions, the operation panel 14 outputs, to the control unit 94, an instruction signal corresponding to the instruction inputted by the user.

The processing tank 21 houses an endoscope to which reprocessing processing is applied, and is formed in a recessed shape so as to store a solution such as a cleaning solution, a disinfection solution, a sterilization solution or a rinsing solution.

A water supply hose connecting port 31 is connected to a faucet through a water supply hose H. The water supply hose connecting port 31 is connected to a water supply conduit 32. The water supply conduit 32 is connected to a three-way electromagnetic valve 33. The water supply conduit 32 is provided with a water supply electromagnetic valve 34, a check valve 35, and a water supply filter 36 in this order from the water supply hose connecting port 31 side.

A circulation nozzle 37 communicates with either one of the water supply conduit 32 or a solution feeding conduit 38 by a switching operation of the three-way electromagnetic valve 33. The circulation nozzle 37 discharges, to the processing tank 21, either one of water supplied from the faucet or a solution taken in through a circulation port 40.

The solution feeding conduit 38A is provided with a solution feeding pump 39.

The circulation port 40 is formed at a bottom portion of the processing tank 21, and communicates with an inflow conduit 41. A filter made of a wire mesh or the like is attached to the circulation port 40 for trapping dirt.

The inflow conduit 41 is branched into two portions, and the two branched portions are connected to the solution feeding conduit 38 and a channel conduit 42. The channel conduit 42 is connected to connectors 43. The channel conduit 42 is provided with a channel pump 44 which feeds a solution or feeds air, a channel block 45, and an electromagnetic valve 46. A water leakage detection connector 47 is connected to a water leakage detection pump 49 through a water leakage detection conduit 48. The channel conduit 42 is connected also to a conduit for case 52 including a relief valve 51. The conduit for case 52 is connected to an accessory case 54 through a tank bottom nozzle 53.

The endoscope reprocessor 1 circulates a solution by taking in the solution in the processing tank 21 through the circulation port 40 and by discharging the solution from the circulation nozzle 37, the connectors 43 and the tank bottom nozzle 53.

An alcohol tank 61 is connected to the channel block 45 through an alcohol conduit 62. Alcohol is stored in the alcohol tank 61. The alcohol conduit 62 is provided with an alcohol pump 63 and an electromagnetic valve 64.

A detergent tank 65 is connected to a detergent nozzle 67 through a detergent conduit 66. A detergent is stored in the detergent tank 65. The detergent conduit 66 is provided with a detergent pump 68.

An air feeding pump 71 is connected to the channel block 45 through an air feeding conduit 72. The air feeding conduit 72 is provided with a check valve 73 and an air filter 74. The air feeding pump 71 takes in air from the outside, and feeds air to the channel block 45.

A solution discharge port 81 is formed at the bottom portion of the processing tank 21. The solution discharge port 81 is connected to a disinfection solution tank 82 and external solution discharge means Ed through solution discharge valves 81a, 81b which open or close the solution discharge port 81. The solution discharge port 81 discharges a solution in the processing tank 21 to the external solution discharge means Ed through the solution discharge valve 81a and a solution discharge conduit 83 by the solution discharge pump 84 being driven. Further, the solution discharge port 81 allows a disinfection solution in the processing tank 21 to be discharged to the disinfection solution tank 82 through the solution discharge valve 81b and a collecting conduit 85 such that the disinfection solution can be collected.

The disinfection solution tank 82 stores a disinfection solution. The disinfection solution in the disinfection solution tank 82 is heated by a heating unit 86.

A disinfection solution nozzle 87 is connected to the disinfection solution tank 82 through a supply conduit 88. The supply conduit 88 is provided with a disinfection solution filter 89 and a disinfection solution pump 90. The disinfection solution nozzle 87 discharges the disinfection solution in the disinfection solution tank 82 into the processing tank 21 by the disinfection solution pump 90 being driven.

An ultrasound vibration unit 91, a heater 92, and a temperature detection sensor 93 are disposed at the bottom portion of the processing tank 21.

The control unit 94 controls respective parts in the endoscope reprocessor 1. The control unit 94 includes a memory 95 and a processor 96. Functions of the control unit 94 are realized by the processor 96 reading programs stored in the memory 95 and executing the programs.

Configuration of Medicinal Solution Supply Mechanism D

Next, a configuration of a medicinal solution supply mechanism D of the endoscope reprocessor 1 is described.

Figure 2:
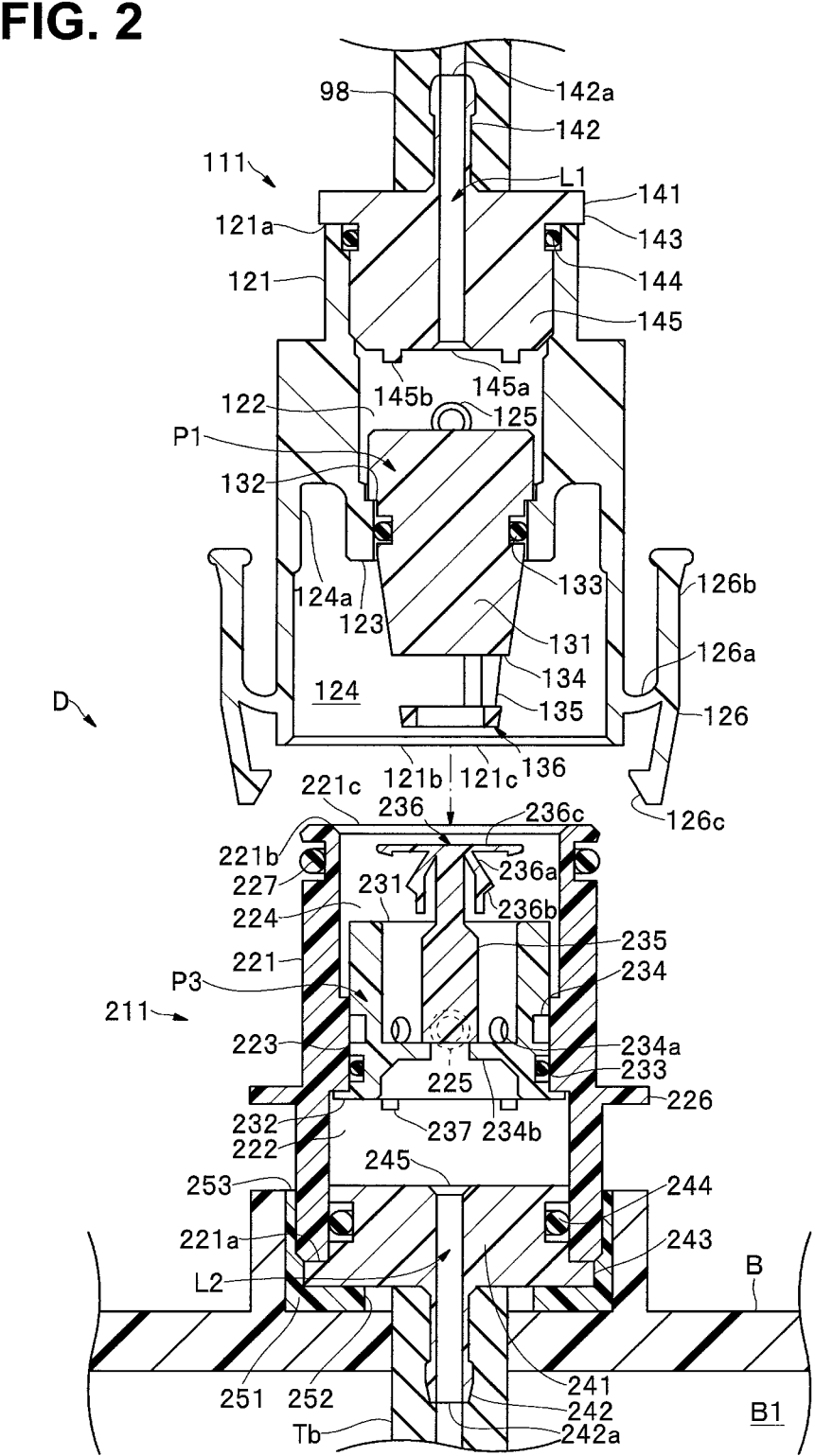
FIG. 2 is a cross-sectional view showing one example of a configuration of a medicinal solution supply mechanism in the endoscope reprocessor according to the embodiment of the present invention.
Figure 3:
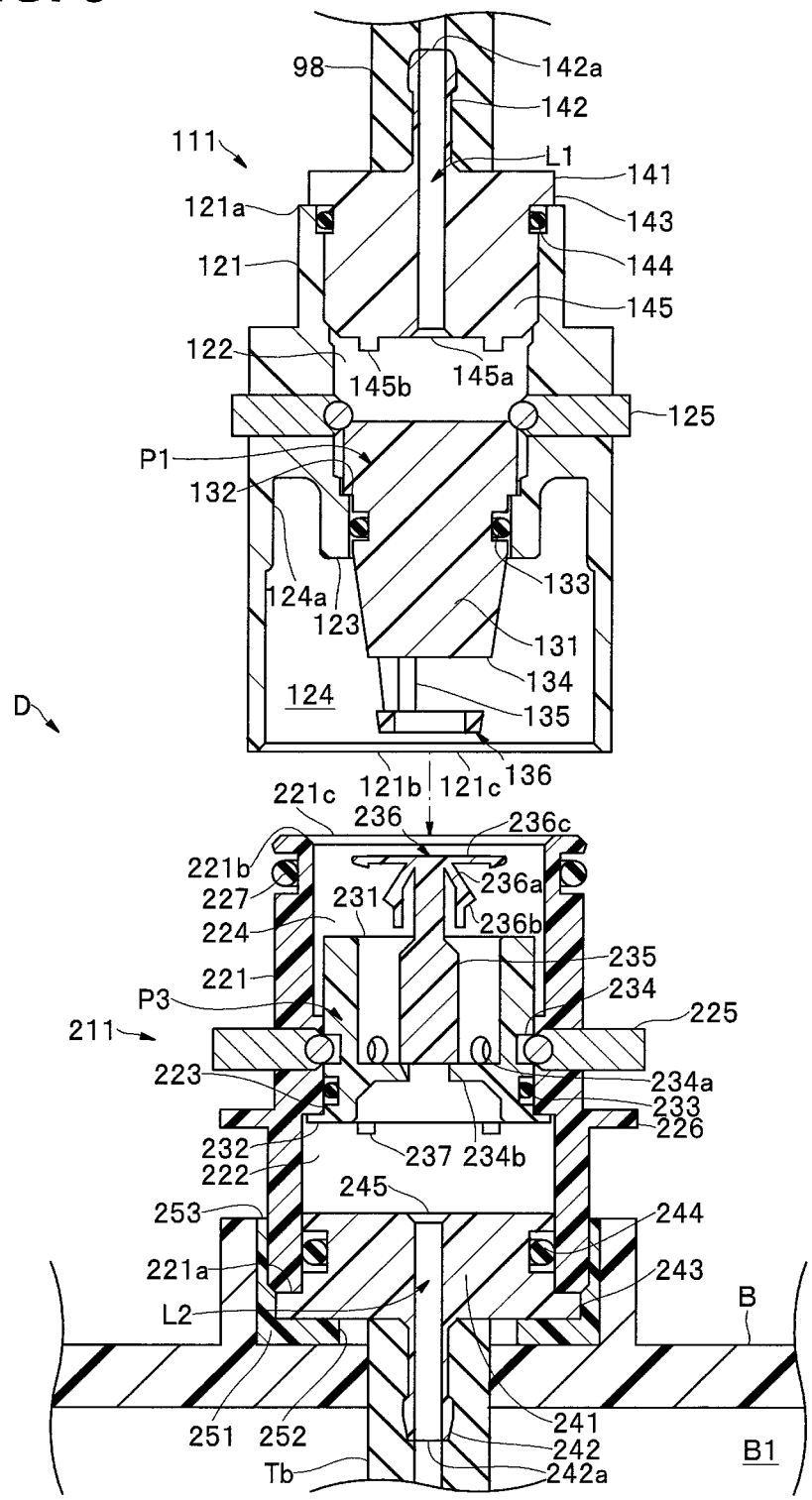
FIG. 3 is a cross-sectional view showing one example of a configuration of the medicinal solution supply mechanism in the endoscope reprocessor according to the embodiment of the present invention.

FIG. 2 and FIG. 3 are cross-sectional views showing one example of the configuration of the medicinal solution supply mechanism D in the endoscope reprocessor 1. FIG. 3 is a cross-sectional view of the medicinal solution supply mechanism D taken in a direction orthogonal to the cross section in FIG. 2.

The medicinal solution supply mechanism D supplies a medicinal solution to the disinfection solution tank 82. The medicinal solution is, for example, a disinfection solution or a sterilization solution. In the disinfection solution tank 82, besides the disinfection solution collected from the processing tank 21 through the collecting conduit 85, a disinfection solution supplied by the medicinal solution supply mechanism D is also stored. The medicinal solution supply mechanism D may supply a disinfection solution prepared in a predetermined concentration or may supply an undiluted disinfection solution. When an undiluted disinfection solution is supplied, the undiluted disinfection solution is diluted by diluting water in the disinfection solution tank 82 to be adjusted so as to have a predetermined concentration.

The medicinal solution supply mechanism D includes a suction pump 97, a tube 98, a bottle connecting instrument 111 and a bottle B having a nozzle 211. The bottle connecting instrument 111 is connected to the nozzle 211 (FIG. 2 and FIG. 3).

The suction pump 97 is connected to the disinfection solution tank 82. Under the control of the control unit 94, the suction pump 97 sucks the disinfection solution in the bottle B and discharges the disinfection solution into the disinfection solution tank 82.

The tube 98 is made of a material such as rubber, for example. One end of the tube 98 communicates with the suction pump 97, and the other end of the tube 98 is connected to the bottle connecting instrument 111.

As shown in FIG. 2 and FIG. 3, the bottle connecting instrument 111 is made of a material such as resin, for example. The bottle connecting instrument 111 is mounted to the nozzle 211 of the bottle B. The bottle connecting instrument 111 includes a cylindrical body 121, a first advancing and retracting portion 131, and a tube connecting portion 141.

In the cylindrical body 121, one end portion 121a and the other end portion 121b on a side opposite to the one end portion 121a communicate with each other. An insertion port 121c is formed at the other end portion 121b. The cylindrical body 121 includes a one end side inner peripheral portion 122, an inner ring portion 123, an other end side inner peripheral portion 124, a resistance member 125, and a locking member 126.

The one end side inner peripheral portion 122 extends from an inner edge of the one end portion 121a in the other end direction. The one end side inner peripheral portion 122 has a smaller inner diameter than the other end side inner peripheral portion 124.

Inside the cylindrical body 121, the inner ring portion 123 extends from the one end side inner peripheral portion 122 in the other end direction and inwardly in the radial direction. The inner ring portion 123 has a smaller inner diameter than the one end side inner peripheral portion 122.

The other end side inner peripheral portion 124 extends from the insertion port 121c in one end direction. The other end side inner peripheral portion 124 has a larger inner diameter than the one end side inner peripheral portion 122. A deep portion of the other end side inner peripheral portion 124 extends inwardly in a radial direction and intersects with an outer peripheral surface of the inner ring portion 123. An annular groove 124a is formed between the outer peripheral surface of the inner ring portion 123 and the other end side inner peripheral portion 124.

The resistance member 125 is formed of plungers each of which includes a ball and a spring which biases the ball, for example. The resistance member 125 generates a contact resistance Ra between the resistance member 125 and the first advancing and retracting portion 131.

For example, in FIG. 2 and FIG. 3, the resistance member 125 is disposed such that, in the one end side inner peripheral portion 122, the balls are brought into contact with an outer edge on one end side of the first advancing and retracting portion 131 at a position P1. The resistance member 125 may be formed of retaining members such as pins in place of the balls.

The locking member 126 includes: protruding lugs 126a formed so as to protrude from an outer peripheral surface of the cylindrical body 121; tabs 126b formed on one end side of the protruding lugs 126a in an extending manner; and locking pawls 126c formed on the other end side of the protruding lugs 126a in an extending manner.

The first advancing and retracting portion (first advancing and retracting member) 131 is disposed so as to be advanceable and retractable in a first flow path L1 between the position P1 which is a first position and a position P2 which is a second position (see FIG. 7), and opens or closes the first flow path L1. The first advancing and retracting portion 131 includes a stopper 132, a packing 133 which is a sealing member, a frustoconical portion 134, a support member 135, and a first fitting portion 136.

The stopper 132 is disposed inside the one end side inner peripheral portion 122, and has an outer diameter larger than an inner diameter of the inner ring portion 123. The stopper 132 is brought into contact with and is stopped by the inner ring portion 123 thus preventing the falling of the first advancing and retracting portion 131.

The packing 133 is made of a material such as rubber, and has a ring shape. The packing 133 is mounted in a circumferential groove continuously formed on the other end side of the stopper 132. The packing 133 generates a slide resistance Rb between the packing 133 and an inner peripheral surface of the inner ring portion 123.

The frustoconical portion 134 is continuously formed on the other end side of the circumferential groove in which the packing 133 is mounted. The frustoconical portion 134 has an outer diameter that is gradually decreased toward the other end direction.

The support member 135 extends from the frustoconical portion 134 in the other end direction. The length of the support member 135 is preliminarily adjusted to a length allowing a second fitting portion 236 to be housed between the frustoconical portion 134 and the first fitting portion 136.

The first fitting portion (first fitting member) 136 is continuously formed on the other end side of the support member 135. The first fitting portion 136 is formed into a ring shape so as to allow the insertion of the second fitting portion 236. The first fitting portion 136 has a predetermined inner diameter. In other words, the first fitting portion 136 is formed at the first advancing and retracting portion 131 so as to be located on the insertion port 121c side.

The tube connecting portion 141 includes a mounting sleeve 142, an outwardly protruding portion 143, a packing 144 and a barrel portion 145.

The mounting sleeve 142 is formed on one end side of the tube connecting portion 141. The mounting sleeve 142 has an elongated cylindrical shape, and includes a connecting port 142a at an end portion. A slippage stopper may be provided on an outer peripheral surface of the mounting sleeve 142 in the vicinity of the end portion of the mounting sleeve 142. By mounting the tube 98 on the mounting sleeve 142, the connecting port 142a and the tube 98 are connected with each other.

The outwardly protruding portion 143 is continuously formed on the other end side of the mounting sleeve 142, and is formed in a shape protruding outwardly in the radial direction so as to engage with an end surface of the one end portion 121a.

The packing 144 is made of a material such as rubber, and has a ring shape. The packing 144 is mounted in a circumferential groove continuously formed on the other end side of the outwardly protruding portion 143, and is brought into close contact with the cylindrical body 121.

The barrel portion 145 is disposed inside the one end side inner peripheral portion 122, and extends from the other end side of the circumferential groove in which the packing 144 is mounted. The barrel portion 145 includes, on an end surface thereof, the other end opening 145a which communicates with the connecting port 142a through an inner flow path. A protruding portion 145b is formed around the other end opening 145a, thereby forming a gap between the end surface of the barrel portion 145 and the first advancing and retracting portion 131.

The bottle B is made of a material such as resin, for example. In the bottle B, a medicinal solution is stored in a medicinal solution storing unit B1 (medicinal solution storing chamber in the bottle B). Although the bottle B has a quadrangular box shape, for example, the shape of the bottle B is not limited to such a shape, but the bottle B may have other shapes such as a circular cylindrical shape. Further, the bottle B may have a grasping portion for enabling the bottle B to be carried.

The nozzle 211 is provided on an outer wall of the bottle B, and communicates with the medicinal solution storing unit B1 through a bottle tube Tb. A distal end of the nozzle 211 is inserted into the insertion port 121c. The nozzle 211 includes a nozzle sleeve 221, a second advancing and retracting portion 231, a storing unit connecting portion 241, and a cap 251.

In the nozzle sleeve 221, a proximal end portion 221a and a distal end portion 221b on a side opposite to the proximal end portion 221a communicate with each other. A nozzle opening 221c is formed at the distal end portion 221b. The distal end portion 221b has an outer diameter smaller than an inner diameter of the other end side inner peripheral portion 124 and hence, the distal end portion 221b is insertable into the insertion port 121c. The nozzle sleeve 221 includes a proximal end side inner peripheral portion 222, a small inner peripheral portion 223, a distal end side inner peripheral portion 224, a resistance member 225, projections 226, and a packing 227.

The proximal end side inner peripheral portion 222 extends from an inner edge of the proximal end portion 221a in a distal end direction.

The small inner peripheral portion 223 extends from the proximal end side inner peripheral portion 222 in the distal end direction. The small inner peripheral portion 223 has a smaller inner diameter than the proximal end side inner peripheral portion 222 and the distal end inner peripheral portion 224.

The distal end side inner peripheral portion 224 extends from the small inner peripheral portion 223 in the distal end direction, and communicates with the nozzle opening 221c.

The resistance member 225 is formed of plungers each of which includes a ball and a spring which biases the ball, for example. The resistance member 225 generates a contact resistance Rc between the second retaining member and the second advancing and retracting portion 231.

For example, in FIG. 2 and FIG. 3, the resistance member 225 is disposed such that the balls advance into a circumferential recessed portion 234 of the second advancing and retracting portion 231 at a position P3 in the small inner peripheral portion 223.

The projections 226 are formed so as protrude from an outer peripheral surface of the nozzle sleeve 221, to enable locking by the locking pawls 126c.

The packing 227 is made of a material such as rubber, and is formed in a ring shape. The packing 227 is mounted in a circumferential groove formed on the outer peripheral surface of the nozzle sleeve 221 at a position in the vicinity of the distal end portion 221b, and the packing 227 slidably moves on an inner surface of the annular groove 124a.

In the nozzle sleeve 221, the second advancing and retracting portion (second advancing and retracting member) 231 moves to advance and retract between the position P3 which is a third position and a position P4 which is a fourth position (see FIG. 7) so as to open or close a second flow path L2. The second advancing and retracting portion 231 has a cylindrical shape. The second advancing and retracting portion 231 includes a stopper 232, a packing 233, a circumferential recessed portion 234, a support pillar 235, the second fitting portion 236 and protruding portions 237.

The stopper 232 is disposed inside the proximal end side inner peripheral portion 222. The stopper 232 has a larger outer diameter than the small inner peripheral portion 223, and is brought into contact with and is stopped by the small inner peripheral portion 223, thus preventing the falling of the second advancing and retracting portion 231.

The packing 233 is made of a material such as rubber, and has a ring shape. The packing 233 is mounted in a circumferential groove continuously formed on a distal end side of the stopper 232. The packing 233 generates a slide resistance Rd between the packing 233 and an inner peripheral surface of the small inner peripheral portion 223.

The circumferential recessed portion 234 is continuously formed on a distal end side of the circumferential groove in which the packing 233 is mounted. The circumferential recessed portion 234 includes, on the bottom portion thereof, through holes 234a which penetrate an inner peripheral portion. A closure wall 234b which closes the inner peripheral portion is continuously formed on the proximal end side of the through holes 234a.

The support pillar 235 is disposed on the distal end side of the closure wall 234b. The length of the support pillar 235 is preliminarily adjusted to a length so that the second fitting portion 236 is fitted with the first fitting portion 136 in a state where the bottle connecting instrument 111 and the nozzle 211 are connected with each other, the first advancing and retracting portion 131 is positioned at the position P2, and the second advancing and retracting portion 231 is positioned at the position P4.

Figure 4:
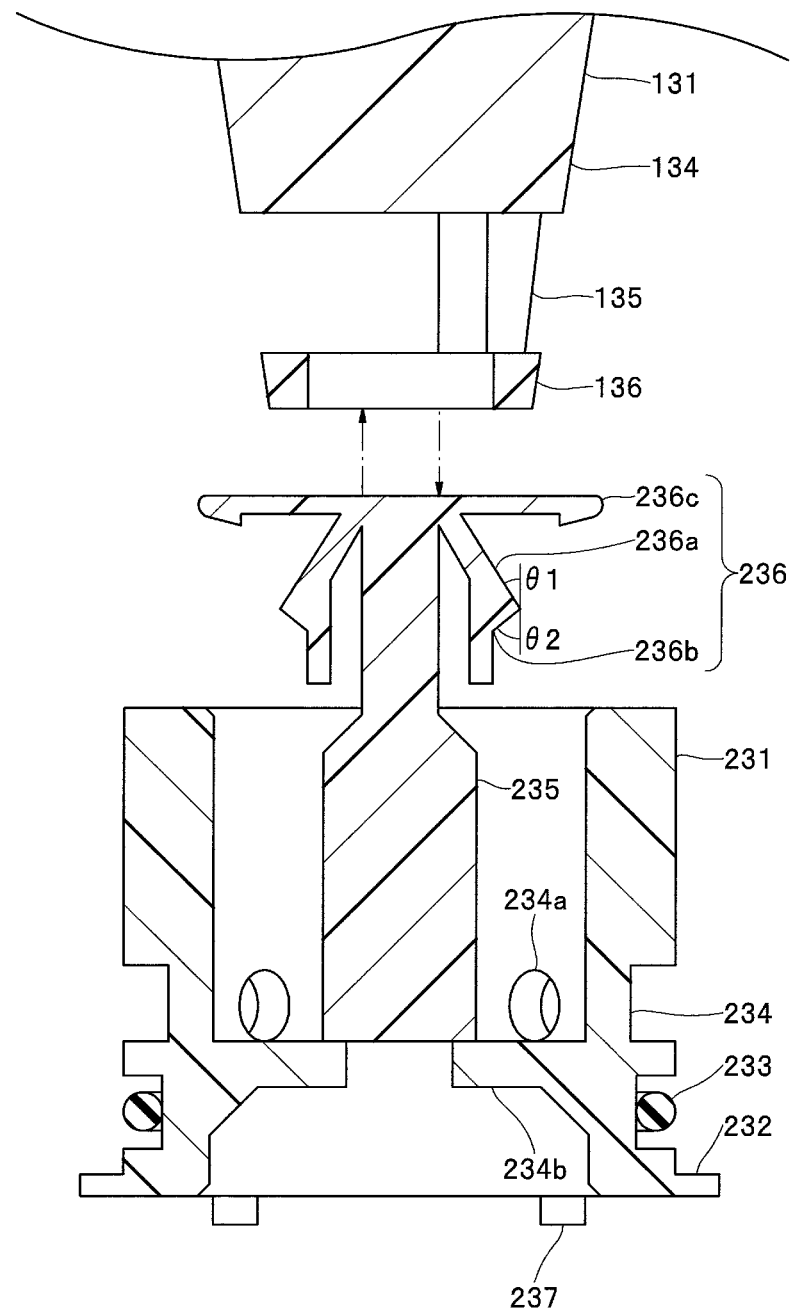
FIG. 4 is an enlarged cross-sectional view showing one example of configurations of a first fitting portion and a second fitting portion in the medicinal solution supply mechanism of the endoscope reprocessor according to the embodiment of the present invention.

FIG. 4 is an enlarged cross-sectional view showing one example of configurations of the first fitting portion 136 and the second fitting portion 236.

As shown in FIG. 4, the second fitting portion (second fitting member) 236 is continuously formed on the distal end side of the support pillar 235, protruded from the second advancing and retracting portion 231 toward a nozzle opening 221c of the nozzle 211, and fitted with the first fitting portion 136. The second fitting portion 236 has a distal end side lug 236a, a proximal end side lug 236b and a contact stop portion 236c.

The distal end side lug 236a, at a position where the distal end side lug 236a contacts an inner edge of the other end side of the first fitting portion 136, extends so as to be away from the support pillar 235 as the distal end side lug 236a extends from the distal end toward the proximal end of the support pillar 235.

The proximal end side lug 236b, at a position where the proximal end side lug 236b contacts an inner edge of one end side of the fitted first fitting portion 136, extends so as to approach closer to the support pillar 235, as the proximal end side lug 236b extends from the distal end side lug 236a toward the proximal end. The proximal end side lug 236b may extend in the proximal end direction along the inner peripheral portion of the fitted first fitting portion 136.

The contact stop portion 236c, at a position where the contact stop portion 236c is in contact with and is stopped by the frustoconical portion 134, extends from the distal end side of the support pillar 235 outwardly in the radial direction.

An insertion resistance Ri, which is generated when the second fitting portion 236 is inserted into the first fitting portion 136, changes according to an inclination angle $\theta 1$ of the distal end side lug 236a with respect to the insertion direction.

An extraction resistance Ro, which is generated when the second fitting portion 236 is extracted from the first fitting portion 136, changes according to an inclination angle $\theta 2$ of the proximal end side lug 236b with respect to the extraction direction.

The extraction resistance Ro is set to be larger than the respective moving resistances R1, R2 such that the first advancing and retracting portion 131 moves to the position P1 and the second advancing and retracting portion 231 moves to the position P3 by extracting the second fitting portion 236 from the first fitting portion 136.

More specifically, the inclination angle $\theta 2$ is set such that the extraction resistance Ro becomes larger than the respective moving resistances R1, R2.

Characteristics such as a frictional force and a side pressure of the packings 133, 233 and a frictional force, a biasing force and the like of the resistance members 125, 225 may be wholly or partially set so as to make the respective moving resistances R1, R2 smaller than the extraction resistance Ro.

In order to enable the connection between the bottle connecting instrument 111 and the nozzle 211 with a smaller force, it is desirable that the inclination angles $\theta 1$, $\theta 2$ are set to $\theta 1 < \theta 2$ so as to make the insertion resistance Ri smaller than the extraction resistance Ro.

The protruding portions 237 are formed on the proximal end surface of the second advancing and retracting portion 231, thereby forming a gap between the proximal end surface of the second advancing and retracting portion 231 and the storing unit connecting portion 241.

The storing unit connecting portion 241 includes a mounting sleeve 242, an outwardly protruding portion 243, a packing 244, and a distal end opening 245.

The mounting sleeve 242 is formed on the proximal end side of the storing unit connecting portion 241. The mounting sleeve 242 has an elongated cylindrical shape, and includes, on the end portion thereof, a bottle tube connecting port 242a. The mounting sleeve 242 includes, on the outer peripheral surface near the end portion thereof, a slippage stopper 242b. One end of the bottle tube Tb is attached to the mounting sleeve 242. The other end of the bottle tube Tb is disposed in the medicinal solution storing unit B1.

The outwardly protruding portion 243 is continuously formed on the distal end side of the mounting sleeve 242, and is formed in a shape protruding outwardly in the radial direction to engage with the end surface of the proximal end portion 221a.

The packing 244 is made of a material such as rubber, and has a ring shape. The packing 244 is mounted in a circumferential groove continuously formed on the distal end side of the outwardly protruding portion 243, and is brought into close contact with the nozzle sleeve 221.

The distal end opening 245 is formed on the distal end surface of the storing unit connecting portion 241. The distal end opening 245 communicates with the bottle tube connecting port 242a.

The cap 251 is mounted on the proximal end portion 221a. The cap 251 has a center hole 252 in which the mounting sleeve 242 is disposed. The cap 251 includes an outer peripheral portion 253 which extends in the distal end direction along the outer peripheral surface of the proximal end portion 221a.

The position P1 is a position where the packing 133 is disposed in the inner ring portion 123. When the first advancing and retracting portion 131 is positioned at the position P1, the packing 133 is brought into close contact with the inner side of the inner ring portion 123, to shut off the first flow path L1, thereby bringing the bottle connecting instrument 111 into a closed state.

At the position P1, the first advancing and retracting portion 131 has a moving resistance R1 which is a combination of a contact resistance Ra and a slide resistance Rb. When the first advancing and retracting portion 131 is positioned at the position P1, the resistance member 125 and the packing 133 configure a first retaining member which retains the first advancing and retracting portion 131. The first retaining member includes the resistance member 125 disposed on the inner periphery of the first flow path L1. The first retaining member applies the moving resistance R1, which is smaller than the extraction resistance Ro generated when the second fitting portion 236 is removed from the first fitting portion 136, to the first advancing and retracting portion 131 at the position P1.

The position P2 is a position where the packing 133 is disposed on the one end side with respect to the inner ring portion 123. When the first advancing and retracting portion 131 is positioned at the position P2, a gap is formed between the first advancing and retracting portion 131 and the inner ring portion 123, to allow the communication of the first flow path L1, thereby bringing the bottle connecting instrument 111 into an open state.

The first flow path L1 is configured by the other end side inner peripheral portion 124, the gap between the first advancing and retracting portion 131 and the inner ring portion 123, the gap between the first advancing and retracting portion 131 and the one end side inner peripheral portion 122, the gap between the barrel portion 145 and the first advancing and retracting portion 131, and the inner flow path of the tube connecting portion 141. The first flow path L1 connects the connecting port 142a and the insertion port 121c with each other.

The first advancing and retracting portion 131 is disposed so as to be advanceable and retractable in the first flow path L1. When the first advancing and retracting portion 131 is positioned at the first position P1 in the first flow path L1, the first advancing and retracting portion 131 shuts off the first flow path L1. When the first advancing and retracting portion 131 is positioned at the second position on the connecting port 142a side with respect to the first position P1, the first advancing and retracting portion 131 opens the first flow path L1.

The position P3 is a position where the packing 233 is disposed inside the small inner peripheral portion 223. When the second advancing and retracting portion 231 is positioned at the position P3, the packing 233 is in close contact with the inside of the small inner peripheral portion 223, to shut off the second flow path L2, thereby bringing the nozzle 211 into a closed state.

At the position P3, the second advancing and retracting portion 231 has a moving resistance R2 which is a combination of the contact resistance Rc and the slide resistance Rd. When the second advancing and retracting portion 231 is positioned at the position P3, the resistance member 225 and the packing 233 configure a second retaining member which retains the second advancing and retracting portion 231. The second retaining member includes the packing 233 which is a seal member disposed on the outer periphery of the second advancing and retracting portion 231. The second retaining member may be a packing, not shown, which is disposed on the inner periphery of the nozzle 211 in place of the packing 233. The second retaining member applies the moving resistance R2, which is smaller than the extraction resistance Ro, to the second advancing and retracting portion 231 at the position P3.

The position P4 is a position where the packing 233 is disposed on the proximal end side with respect to the small inner peripheral portion 223. When the second advancing and retracting portion 231 is positioned at the position P4, a gap is formed between the second advancing and retracting portion 231 and the small inner peripheral portion 223, to allow the communication of the second flow path L2, thereby bringing the nozzle 211 into an open state.

The second flow path L2 is configured by the storing unit connecting portion 241, the gap between the storing unit connecting portion 241 and the second advancing and retracting portion 231, the gap between the second advancing and retracting portion 231 and the proximal end side inner peripheral portion 222, the circumferential recessed portion 234, the through holes 234a, the inside of the second advancing and retracting portion 231, and the distal end side inner peripheral portion 224. The second flow path L2 connects the bottle tube connecting port 242a and the nozzle opening 221c with each other.

The second advancing and retracting portion 231 is disposed so as to be advanceable and retractable in the nozzle 211. When the second advancing and retracting portion 231 is positioned at the third position in the nozzle 211, the second advancing and retracting portion 231 shuts off the nozzle 211. When the second advancing and retracting portion 231 is positioned at the fourth position which is on a medicinal solution storing unit B1 side with respect to the third position, the second advancing and retracting portion 231 opens the nozzle 211.

(Working)

Next, the working of the medicinal solution supply mechanism D of the endoscope reprocessor 1 is described.

As shown in FIG. 2 and FIG. 3, when the first advancing and retracting portion 131 is positioned at the position P1, the bottle connecting instrument 111 is brought into a closed state. When the second advancing and retracting portion 231 is positioned at the position P3, the nozzle 211 is brought into a closed state.

Figure 5:
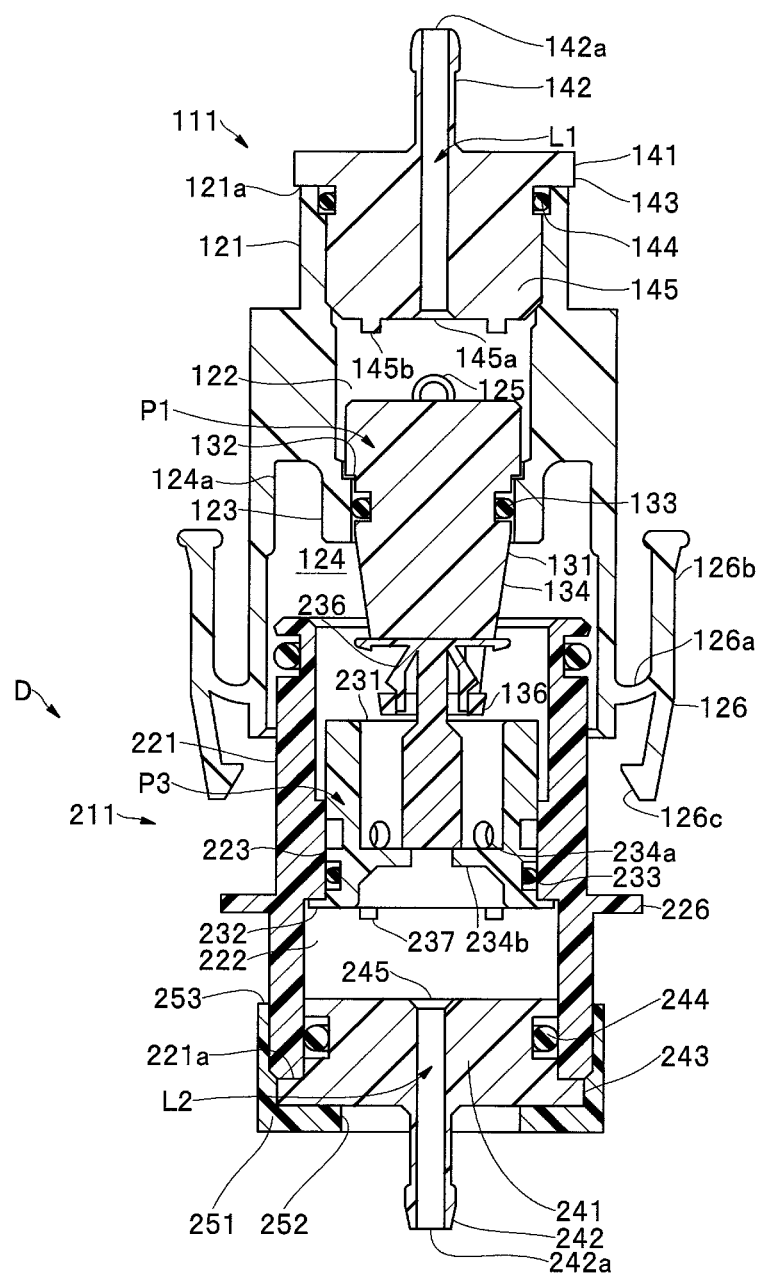
FIG. 5 is a cross-sectional view showing a state where the first fitting portion and the second fitting portion are fitted with each other in the medicinal solution supply mechanism of the endoscope reprocessor according to the embodiment of the present invention.
Figure 6:
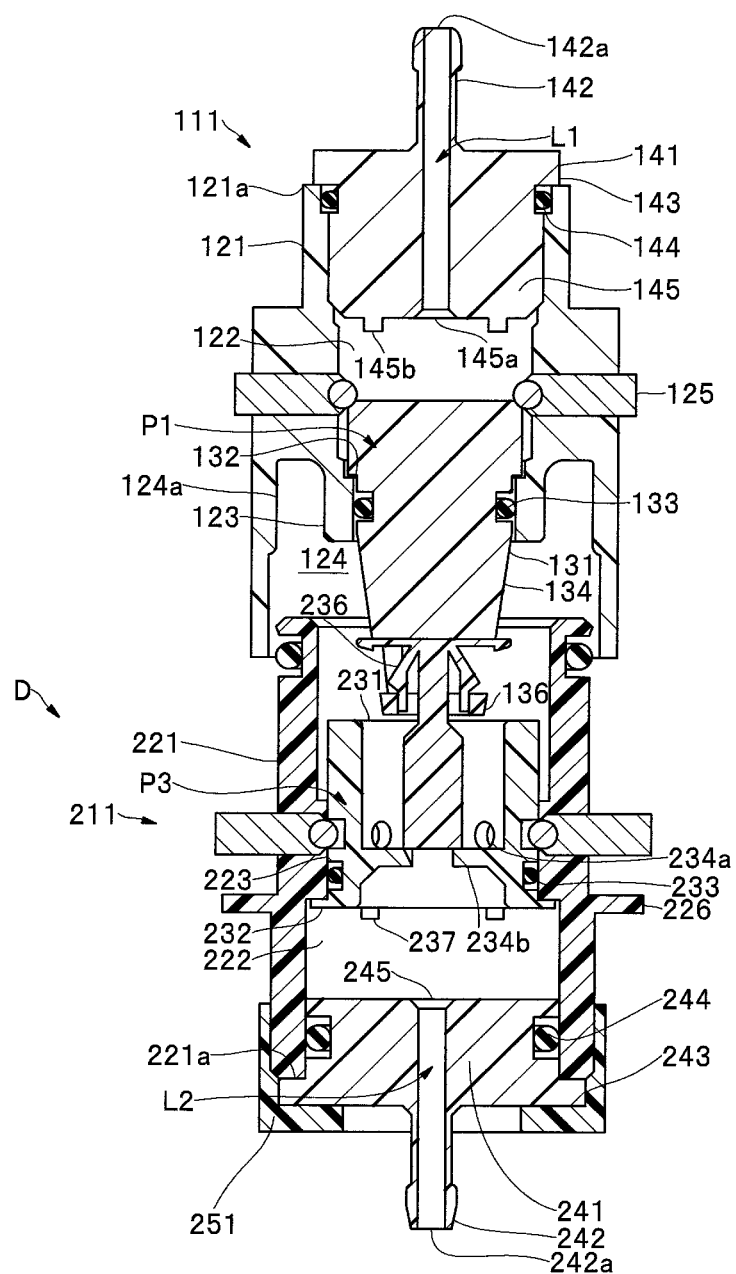
FIG. 6 is a cross-sectional view showing a state where the first fitting portion and the second fitting portion are fitted with each other in the medicinal solution supply mechanism of the endoscope reprocessor according to the embodiment of the present invention.

FIG. 5 and FIG. 6 are cross-sectional views showing a state where the first fitting portion 136 and the second fitting portion 236 are fitted with each other in the medicinal solution supply mechanism D. FIG. 6 is a cross-sectional view of the medicinal solution supply mechanism D taken in the direction orthogonal to the cross section in FIG. 5.

When the bottle connecting instrument 111 is fitted in the nozzle 211, the second fitting portion 236 is pushed to be in contact with the first fitting portion 136. When the bottle connecting instrument 111 is further pushed into the nozzle 211 by an inserting force which exceeds the insertion resistance Ri, the second fitting portion 236 elastically deforms and a lateral width of the second fitting portion 236 becomes small, and the second fitting portion 236 is inserted into the first fitting portion 136. When the second fitting portion 236 passes through the first fitting portion 136, as shown in FIG. 5 and FIG. 6, the second fitting portion 236 restores from the elastically deformed state between the frustoconical portion 134 and the first fitting portion 136, to be fitted with the first fitting portion 136.

In FIG. 5 and FIG. 6, the insertion resistance Ri is set smaller than the respective moving resistances R1, R2, and the second fitting portion 236 is inserted into the first fitting portion 136 before the first advancing and retracting portion 131 and the second advancing and retracting portion 231 move. The insertion resistance Ri may be set larger than the respective moving resistances R1, R2, and the second fitting portion 236 may push and move the first advancing and retracting portion 131 and the second advancing and retracting portion 231 before the second fitting portion 236 is inserted into the first fitting portion 136.

Figure 7:
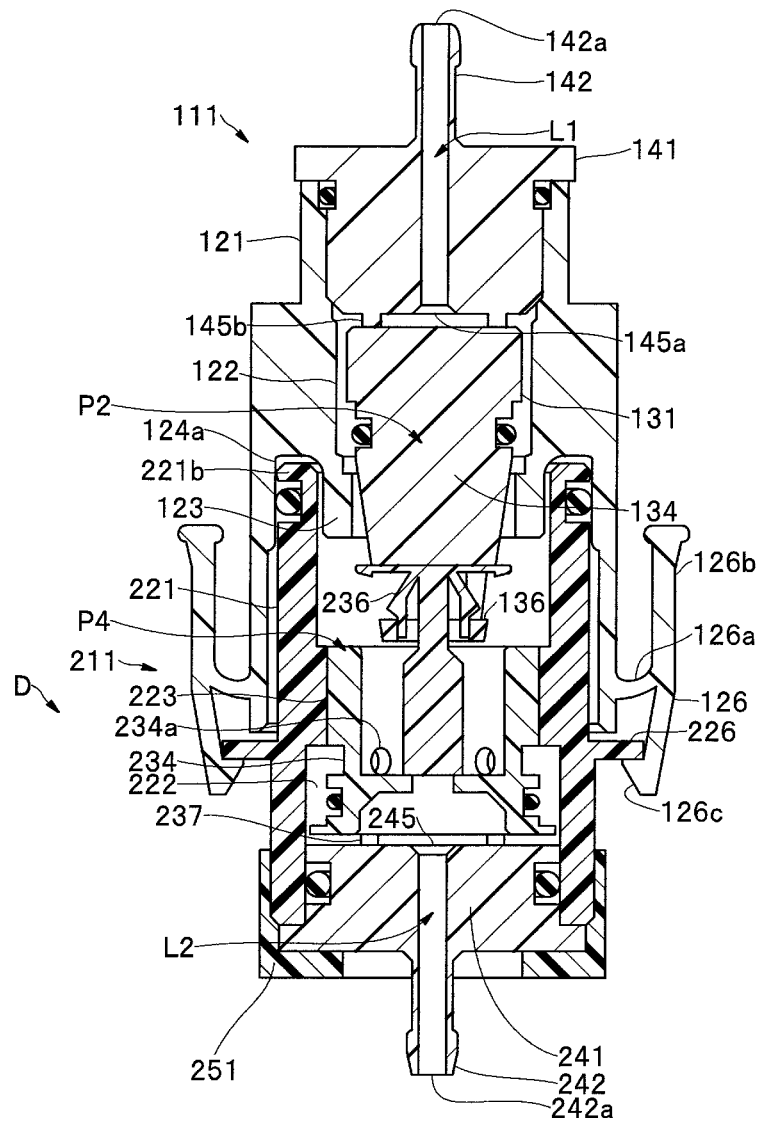
FIG. 7 is a cross-sectional view showing one example of a state where a bottle connecting instrument and a nozzle are connected with each other in the medicinal solution supply mechanism of the endoscope reprocessor according to the embodiment of the present invention.

FIG. 7 is a cross-sectional view showing one example of the state where the bottle connecting instrument 111 and the nozzle 211 are connected with each other.

As shown in FIG. 7, after the first fitting portion 136 and the second fitting portion 236 are fitted with each other, if the bottle connecting instrument 111 is further pushed into the nozzle 211, the first advancing and retracting portion 131 moves from the position P1 to the position P2, to thereby bring the bottle connecting instrument 111 into an open state. The second advancing and retracting portion 231 moves from the position P3 to the position P4, to thereby bring the nozzle 211 into an open state.

When the distal end portion 221b is inserted into the annular groove 124a, the packing 227 is brought into close contact with the inner surface of the annular groove 124a, thereby allowing the inside of the bottle connecting instrument 111 and the inside of the nozzle 211 to be water-tightly or air-tightly sealed from the outside.

When the locking pawls 126c lock the projections 226, the bottle connecting instrument 111 is fixed to the nozzle 211 so as to prevent the falling of the bottle connecting instrument 111.

Figure 8:
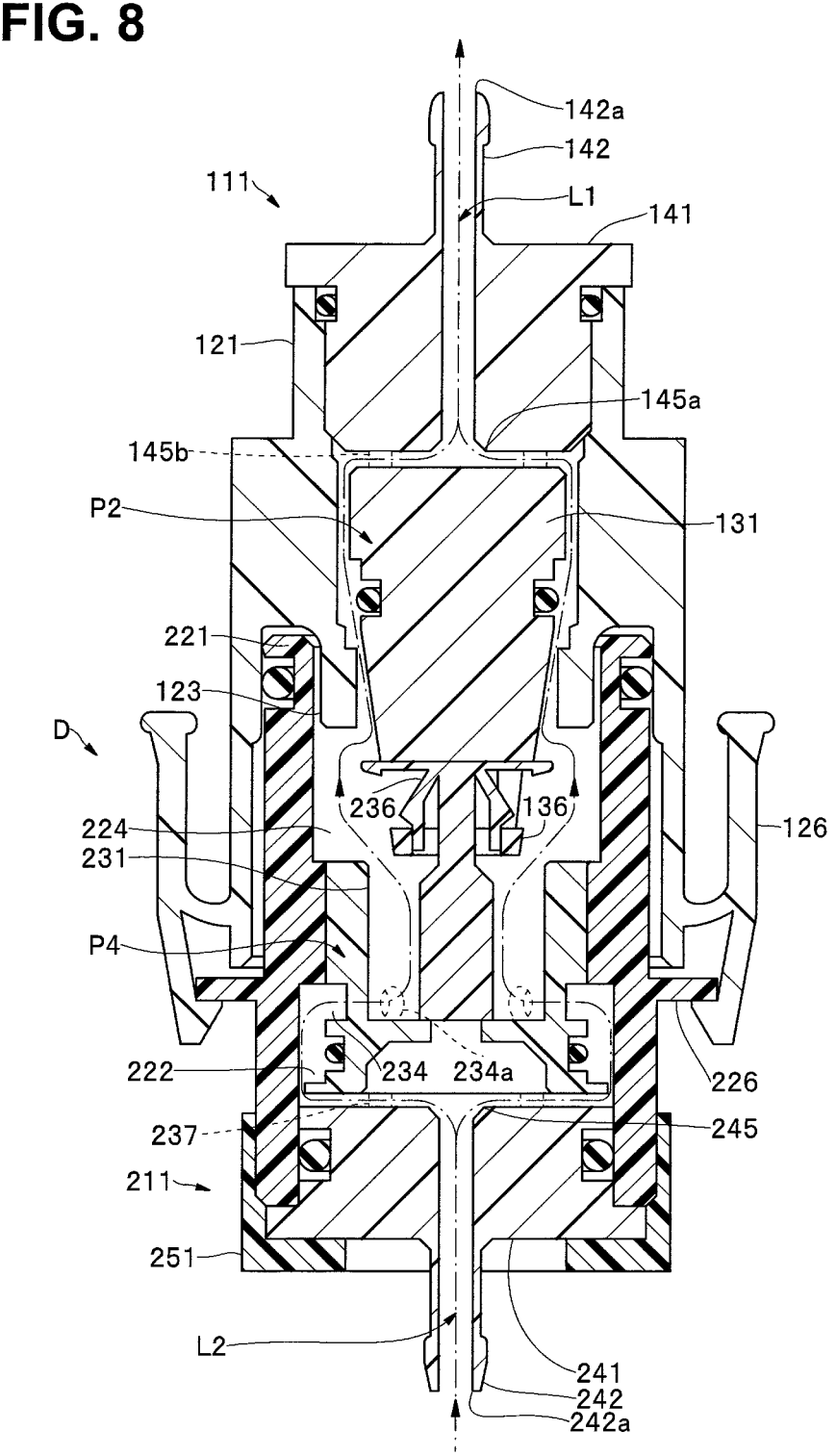
FIG. 8 is a cross-sectional view for describing one example of a first flow path and a second flow path in the medicinal solution supply mechanism of the endoscope reprocessor according to the embodiment of the present invention.

FIG. 8 is a cross-sectional view for describing one example of the first flow path L1 and the second flow path L2.

As shown in FIG. 8, when the bottle connecting instrument 111 and the nozzle 211 are connected with each other, the connecting port 142a and the bottle tube connecting port 242a communicate with each other by the first flow path L1 and the second flow path L2.

When the bottle connecting instrument 111 is separated from the nozzle 211, since the extraction resistance Ro is set to be larger than the respective moving resistances R1, R2, before the second fitting portion 236 is extracted from the first fitting portion 136, the first advancing and retracting portion 131 moves from the position P2 to the position P1, and the second advancing and retracting portion 231 moves from the position P4 to the position P3 (see FIG. 5 and FIG. 6). When the bottle connecting instrument 111 is further separated from the nozzle 211, the stopper 132 is brought into contact with and is stopped by the inner ring portion 123, the stopper 232 is brought into contact with and is stopped by the small inner peripheral portion 223, and the second fitting portion 236 is extracted from the first fitting portion 136 by an extracting force which exceeds the extraction resistance Ro. Accordingly, when the bottle connecting instrument 111 is removed, the bottle connecting instrument 111 and the nozzle 211 are each brought into a closed state, and a leakage of residual solution is prevented.

In FIG. 2, the first advancing and retracting portion 131 is positioned at the position P1. However, even when the first advancing and retracting portion 131 is at the position P2, the bottle connecting instrument 111 can be connected to the nozzle 211.

Figure 9:
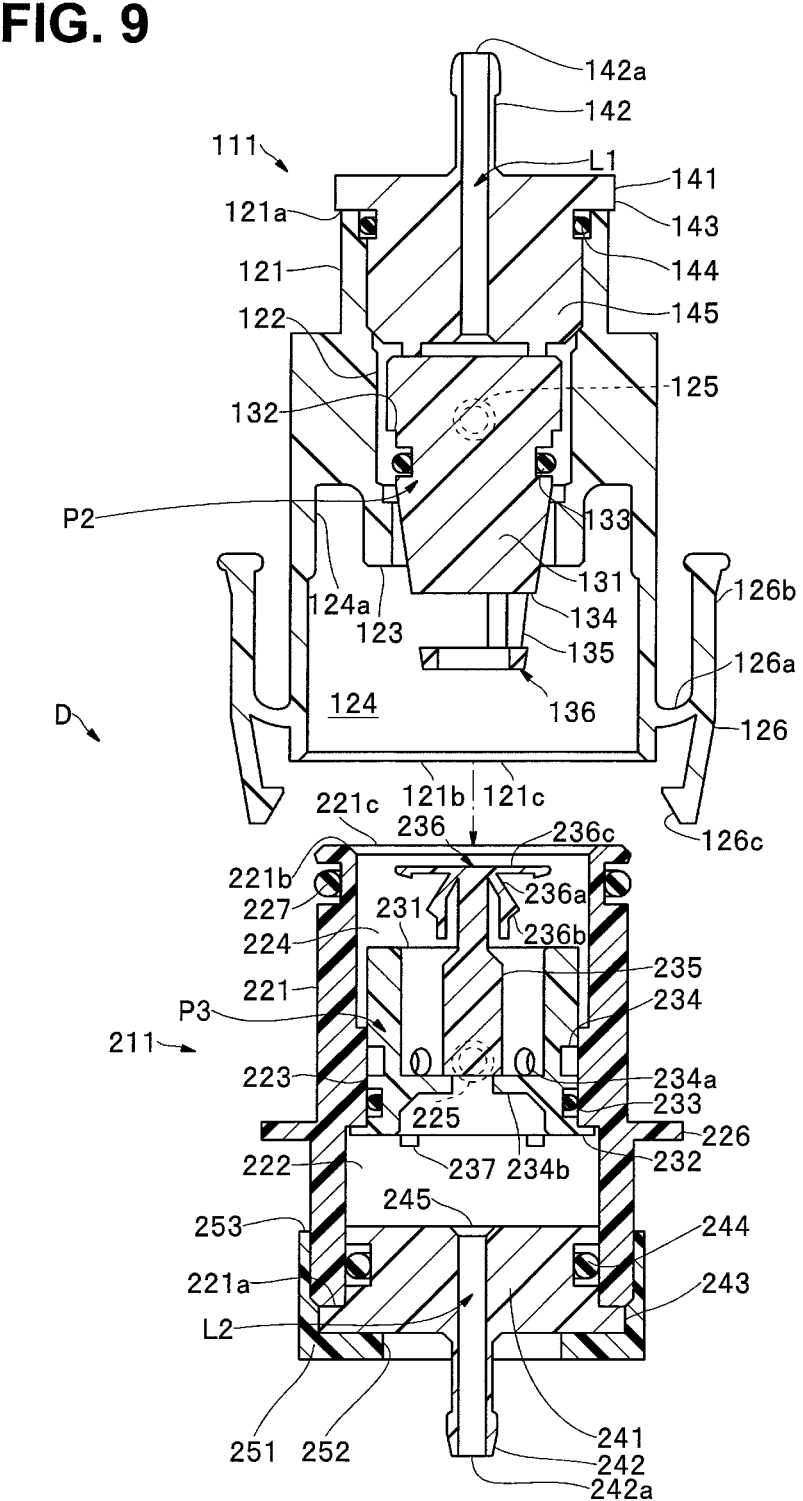
FIG. 9 is a cross-sectional view showing one example of a state where a first advancing and retracting portion is positioned at a second position in the medicinal solution supply mechanism of the endoscope reprocessor according to the embodiment of the present invention.

FIG. 9 is a cross-sectional view showing one example of the state where the first advancing and retracting portion 131 is positioned at the position P2.

As shown in FIG. 9, when the bottle connecting instrument 111 is fitted in the nozzle 211, the second fitting portion 236 is pushed to be in contact with the first fitting portion 136. When the bottle connecting instrument 111 is further pushed into the nozzle 211, the first fitting portion 136 and the second fitting portion 236 are fitted with each other. When the bottle connecting instrument 111 is further pushed into the nozzle 211, the second advancing and retracting portion 231 moves to the position P4, the bottle connecting instrument 111 and the nozzle 211 are connected with each other, and the connecting port 142a and the bottle tube connecting port 242a communicate with each other.

When the first advancing and retracting portion 131 is pushed into the bottle connecting instrument 111 from the position P1 to the position P2 by the fingers of a user, a jig, or the like, the first advancing and retracting portion 131 is retained at the position P2. Accordingly, the bottle connecting instrument 111 maintains an open state even in a state where the bottle connecting instrument 111 is not connected with the nozzle 211 such as an inspection step of the manufacturing of the endoscope reprocessor.

The bottle connecting instrument 111 is connectable with the nozzle 211, in either case, where the first advancing and retracting portion 131 is positioned at the position P1 or where at the position P2. Accordingly, for example, after the inspection step is completed, it is unnecessary to return the first advancing and retracting portion 131 from the position P2 to the position P1. Further, even if the first advancing and retracting portion 131 is positioned at the position P1 or at the position P2, after the bottle connecting instrument 111 is connected to the nozzle 211, in response to the removal of the bottle connecting instrument 111 from the nozzle 211, the first advancing and retracting portion 131 moves to the position P1, and shuts off the first flow path L1 thus preventing a leakage of the residual solution.

According to the embodiment, the endoscope reprocessor 1 includes the bottle connecting instrument 111 which can prevent a leakage of residual solution when the endoscope reprocessor 1 is removed from the bottle B and can easily maintain the open state in a state where the bottle connecting instrument 111 is not connected with the bottle B.

Modification 1

In the embodiment, the second fitting portion 236 has a plurality of locking lugs. However, the second fitting portion may be configured by a brush.

Figure 10:
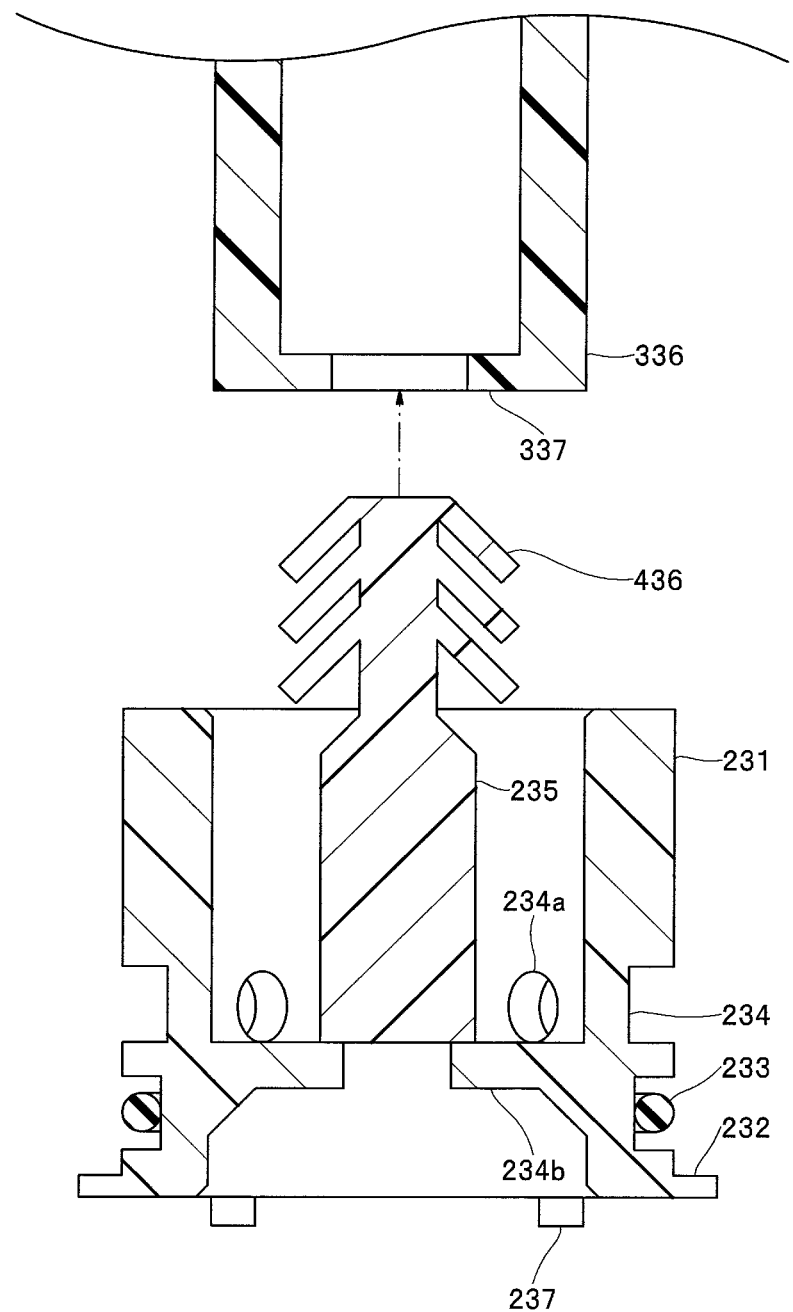
FIG. 10 is an enlarged cross-sectional view showing one example of configurations of a first fitting portion and a second fitting portion in a medicinal solution supply mechanism of an endoscope reprocessor according to a modification 1 of the embodiment of the present invention.
Figure 11:
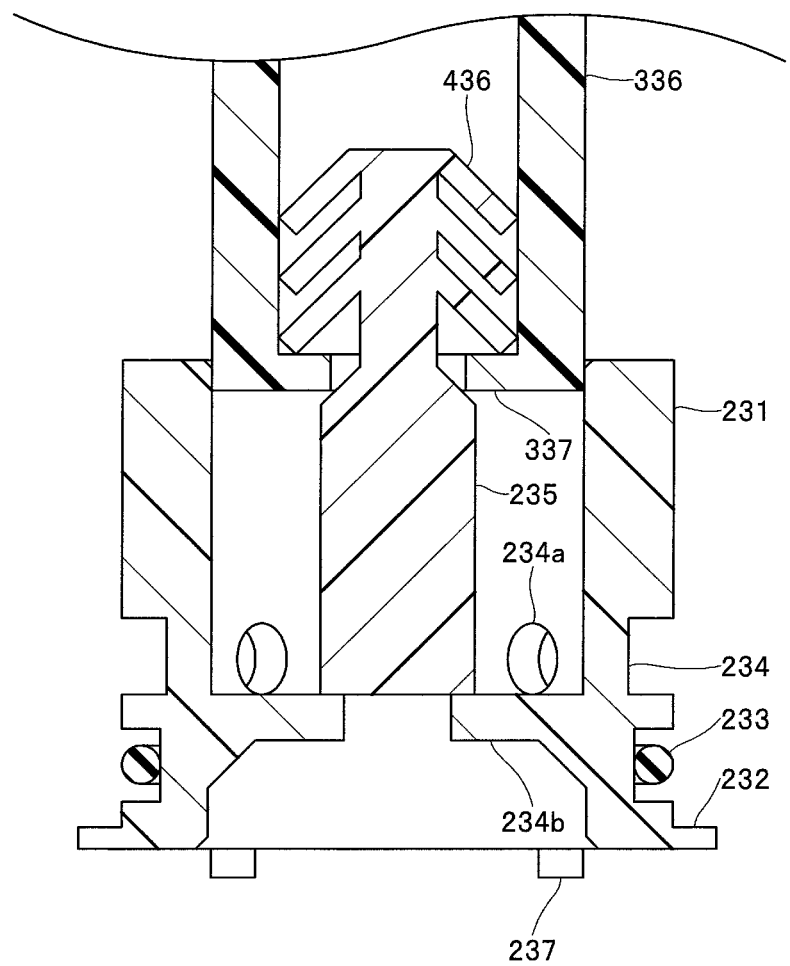
FIG. 11 is a cross-sectional view showing a state where a first fitting portion and a second fitting portion are fitted with each other in the medicinal solution supply mechanism of the endoscope reprocessor according to the modification 1 of the embodiment of the present invention.

FIG. 10 is an enlarged cross-sectional view showing one example of configurations of a first fitting portion 336 and a second fitting portion 436 according to a modification 1 of the embodiment. FIG. 11 is a cross-sectional view showing the state where the first fitting portion 336 and the second fitting portion 436 are fitted with each other. In the present modification, the description of the components which are the same as those in other embodiments and modifications is omitted.

As shown in FIG. 10, the first fitting portion 336 has a cylindrical shape. An inwardly extending flange 337 is formed on the other end of the first fitting portion 336.

The second fitting portion 436 has a brush where distal ends of bristles are directed toward the proximal end of the second fitting portion 436.

As shown in FIG. 11, in the second fitting portion 436, the distal ends of the bristles are fallen along the inner edge of the inwardly extending flange 337 by elastic deformation and advance into the first fitting portion 336, and the distal ends of the bristles restore to the original shape and expand in the first fitting portion 336. The distal ends of the bristles of the second fitting portion 436 are latched to the inner side of the inwardly extending flange 337, to generate an extraction resistance Ro which is larger than an insertion resistance Ri.

Modification 2

In the embodiment, a second fitting portion 636 has the plurality of locking lugs. However, the second fitting portion 636 may be a sponge.

Figure 12:
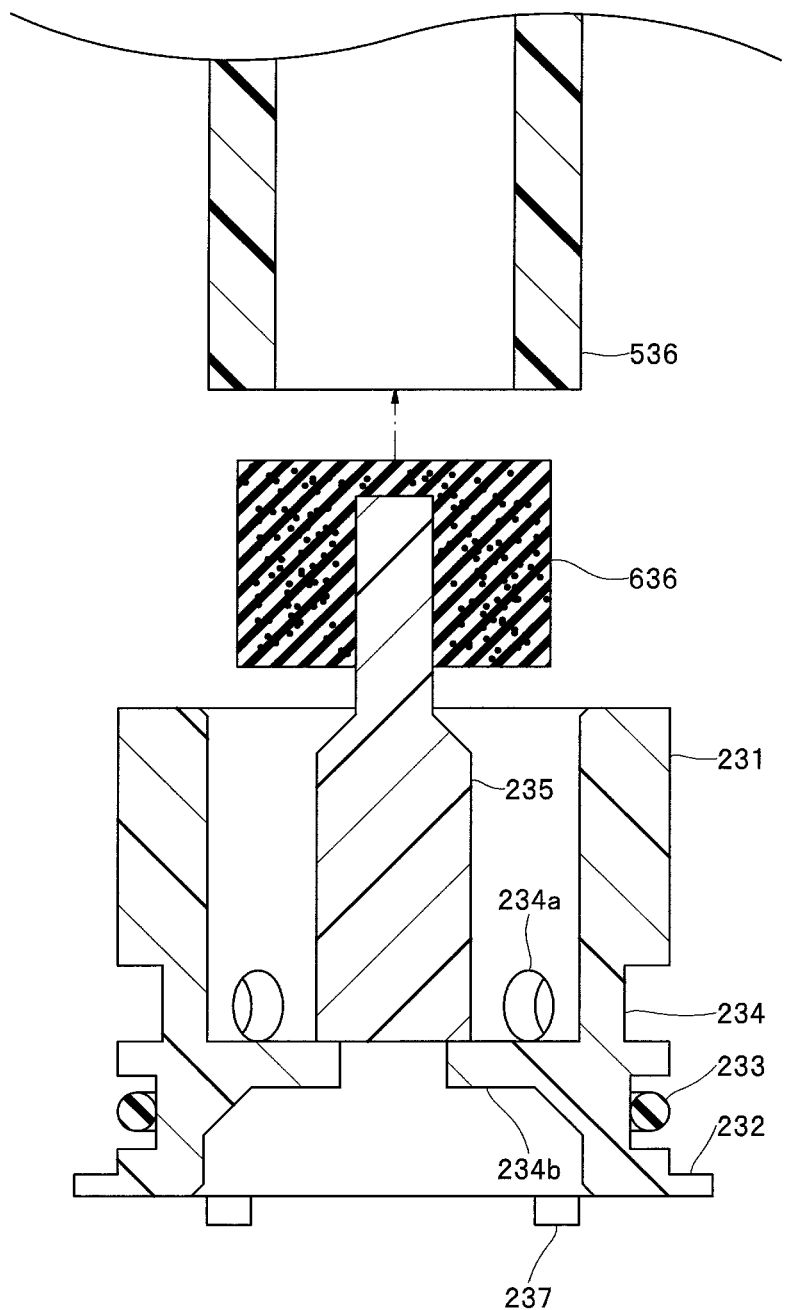
FIG. 12 is an enlarged cross-sectional view showing one example of configurations of a first fitting portion and a second fitting portion in a medicinal solution supply mechanism of an endoscope reprocessor according to a modification 2 of the embodiment of the present invention.
Figure 13:
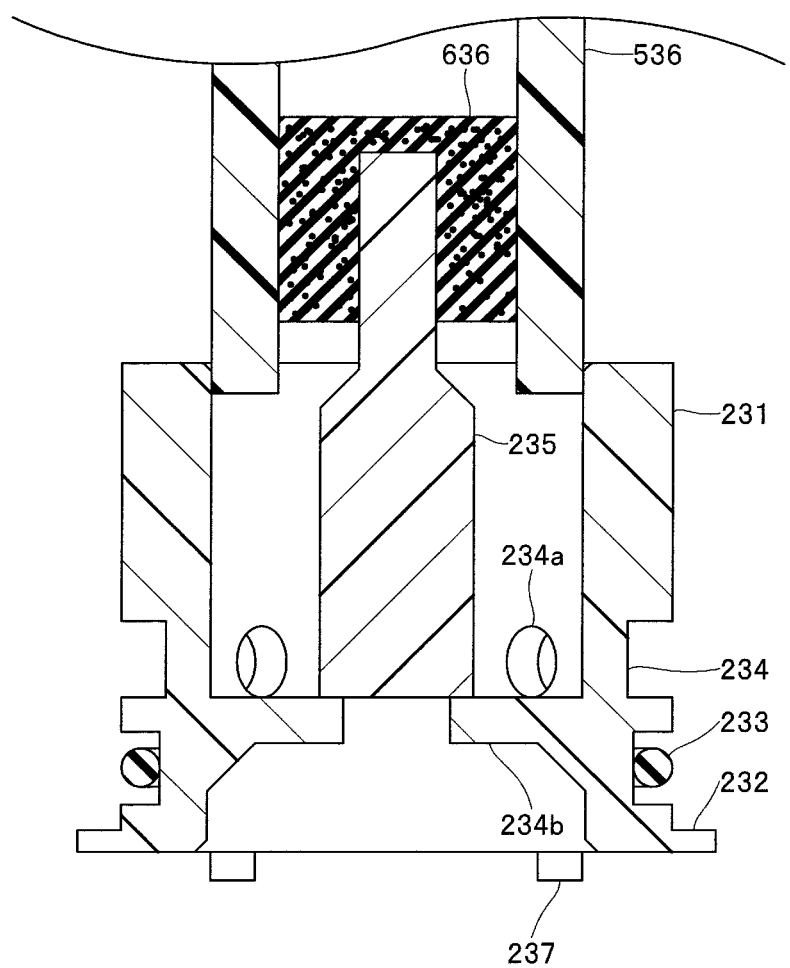
FIG. 13 is a cross-sectional view showing a state where the first fitting portion and the second fitting portion are fitted with each other in the medicinal solution supply mechanism of the endoscope reprocessor according to the modification 2 of the embodiment of the present invention.

FIG. 12 is an enlarged cross-sectional view showing one example of configurations of a first fitting portion 536 and the second fitting portion 636 according to the modification 2 of the embodiment. FIG. 13 is a cross-sectional view showing the state where the first fitting portion 536 and the second fitting portion 636 are fitted with each other. In the present modification, the description of the components which are the same as those in other embodiments and modifications is omitted.

As shown in FIG. 12, the first fitting portion 536 has a cylindrical shape.

The second fitting portion 636 includes a sponge.

As shown in FIG. 12, the second fitting portion 636 is shrunken by elastic deformation and advances into the first fitting portion 536, and water is supplied to the second fitting portion 636 in the first fitting portion 536, to generate an extraction resistance Ro larger than the resistance generated at the time of inserting the second fitting portion 636 into the first fitting portion 536.

The first fitting portions 136, 336, 536 and the second fitting portions 236, 436, 636 are not limited to the configurations in the embodiment and the modifications. The first fitting portions 136, 336, 536 and the second fitting portions 236, 436, 636 may be engaging members or slide members which generate the extraction resistance Ro. For example, the first fitting portions 136, 336, 536 and the second fitting portions 236, 436, 636 may be configured by protruding members and latching members which latch with the protruding members.

In the embodiment and the modifications, the example is described where the resistance members 125, 225 are configured by the plunger. However, the resistance members 125, 225 are not limited to the plunger. The resistance members 125, 225 may be, for example, engaging members or slide members which cooperatively work with the first advancing and retracting portion 131 and the second advancing and retracting portion 231. The resistance members 125, 225 may be provided respectively to the first advancing and retracting portion 131 and the second advancing and retracting portion 231 so as to generate contact resistances Ra, Rc between the resistance members 125, 225 and the one end side inner peripheral portion 122 and the small inner peripheral portion 223, respectively.

In the embodiment and the modifications, the example is described where the medicinal solution is a disinfection solution. However, the medicinal solution is not limited to the disinfection solution. The medicinal solution may be a medicinal solution other than a disinfection solution, such as a cleaning solution and alcohol.

The present invention is not limited to the above-mentioned embodiment, and various modifications, alterations and the like are possible without departing from the gist of the present invention.

What is claimed is:

1. An endoscope reprocessor comprising:
  a main body apparatus including:
    a suction pump;
    a tube having one end which communicates with the suction pump; and
    a bottle connecting instrument connected to another end of the tube; and
  a bottle including:
    a medicinal solution storing chamber; and
      a nozzle which communicates with the medicinal solution storing chamber,
    wherein the bottle connecting instrument includes:
    a connecting port which is connected to the tube;
    an insertion port into which a distal end of the nozzle is inserted;
  a first flow path which connects the connecting port and the insertion port with each other;
  a first advancing and retracting member which is disposed so as to be advanceable and retractable in the first flow path, the first advancing and retracting member being configured to shut off the first flow path when the first advancing and retracting member is positioned at a first position in the first flow path and open the first flow path when the first advancing and retracting member is positioned at a second position on a side of the connecting port with respect to the first position;
  a first fitting member disposed in the first advancing and retracting member on a side of the insertion port; and
  a first retaining member configured to retain the first advancing and retracting member when the first advancing and retracting member is positioned at the first position, and
  the nozzle includes inside of the nozzle:
    a second advancing and retracting member which is disposed so as to be advanceable and retractable in the nozzle, the second advancing and retracting member being configured to shut off the nozzle when the second advancing and retracting member is positioned at a third position in the nozzle and open the nozzle when the second advancing and retracting member is positioned at a fourth position on a side of the medicinal solution storing chamber with respect to the third position;
    a second fitting member which protrudes from the second advancing and retracting member toward a nozzle opening of the nozzle, and is configured to be fitted with the first fitting member; and
    a second retaining member configured to retain the second advancing and retracting member when the second advancing and retracting member is positioned at the third position.

2. The endoscope reprocessor according to claim 1, wherein the first retaining member includes a resistance member disposed on an inner periphery of the first flow path.

3. The endoscope reprocessor according to claim 1, wherein the second retaining member includes a seal member disposed on an inner periphery of the nozzle or on an outer periphery of the second advancing and retracting member.

4. The endoscope reprocessor according to claim 1, wherein
the first retaining member applies a moving resistance to the first advancing and retracting member at the first position, the moving resistance being smaller than an extraction resistance at a time of extracting the second fitting member from the first fitting member, and
the second retaining member applies a moving resistance which is smaller than the extraction resistance to the second advancing and retracting member at the third position.

5. A bottle for use with an endoscope reprocessor, the bottle comprising:
a nozzle provided on an outer wall of the bottle, the nozzle including inside of the nozzle:
an advancing and retracting member disposed so as to be advanceable and retractable in the nozzle, the advancing and retracting member being configured to shut off the nozzle when the advancing and retracting member is positioned at a first position in the nozzle and open the nozzle when the advancing and retracting member is positioned at a second position on an opposite side of a nozzle opening of the nozzle with respect to the first position;
a second fitting member which protrudes from the advancing and retracting member toward the nozzle opening of the nozzle, and is configured to be fitted with a first fitting member of the endoscope reprocessor; and
a retaining member configured to retain the advancing and retracting member when the advancing and retracting member is positioned at the third position,
wherein the advancing and retracting member comprises a stopper configured to limit movement of the advancing and retracting member in a direction toward the nozzle opening; and
the second fitting member includes a distal end side lug, and the distal end side lug extends away from a support pillar of the advancing and retracting member as the distal end side lug extends from a distal end toward a proximal end of the support pillar.

6. The bottle according to claim 5, wherein the retaining member includes a seal member disposed on an inner periphery of the nozzle or on an outer periphery of the advancing and retracting member.

7. The bottle according to claim 5, wherein the retaining member applies a moving resistance to the advancing and retracting member at the first position, the moving resistance being smaller than an extraction resistance at a time of extracting the second fitting member from the first fitting member.

8. The bottle according to claim 5, wherein
the second fitting member includes a proximal end side lug, and
the proximal end side lug extends closer to the support pillar, as the proximal end side lug extends from the distal end side lug toward the proximal end.

9. The bottle according to claim 5, wherein
the second fitting member includes a contact stop portion and extends from the distal end side of the support pillar outwardly in a radial direction.

10. The bottle according to claim 8, wherein each of the distal end side lug and the proximal end side lug has an inclination angle inclined with respect to the support pillar.

11. The bottle according to claim 5, wherein
the nozzle includes a proximal end side inner peripheral portion and a small inner peripheral portion having an inner diameter smaller than the proximal end side inner peripheral portion, and
the stopper is disposed inside the proximal end side inner peripheral portion and has a larger outer diameter than the small inner peripheral portion.

12. The bottle according to claim 5, wherein the second fitting member has an elasticity.

* * * * *